(12) United States Patent
Pennekamp et al.

(10) Patent No.: US 6,413,481 B1
(45) Date of Patent: Jul. 2, 2002

(54) STERILIZATION TUNNEL

(75) Inventors: Ingbert Pennekamp, Crailsheim; Manfred Windsheimer, Satteldorf, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/414,596

(22) Filed: Oct. 8, 1999

(30) Foreign Application Priority Data

Oct. 8, 1998 (DE) .......................................... 198 46 277

(51) Int. Cl.[7] .......................... A61L 2/00; B65G 25/00; B08B 3/00
(52) U.S. Cl. ...................... 422/302; 422/304; 422/295; 422/297; 422/307; 422/308; 134/126; 134/128; 134/133; 198/430; 198/468.01; 198/502.3; 414/148; 414/153; 414/157; 414/166; 414/171; 414/172
(58) Field of Search .................................. 422/291, 292, 422/295, 297, 300, 302, 304–309, 1, 20–21, 24, 26–27, 28, 31–32, 63, 65; 134/126–128, 133; 198/430, 468.1, 502.1, 502.3; 414/147, 148, 150, 153, 157, 158, 166, 171, 172

*Primary Examiner*—Robert J. Warden, Sr.
*Assistant Examiner*—Monzer R. Chorbaji
(74) *Attorney, Agent, or Firm*—Ronald E. Greigg

(57) ABSTRACT

A sterilization tunnel for pharmaceutical containers such as vials has an inlet zone, a sterilization zone, and a cooling zone. A conveyor belt for the vials is disposed inside the sterilization tunnel. An emptying device that can be raised and lowered is disposed in the vicinity of the cooling zone. In order to empty the sterilization tunnel, the frame-shaped emptying device is lowered onto the conveyor belt and then pushes an emptying slider, which is being moved through the sterilization tunnel together with the last vials disposed on the conveyor belt, out from the sterilization tunnel. The emptying device permits a particularly simple operation of the sterilization tunnel.

4 Claims, 2 Drawing Sheets

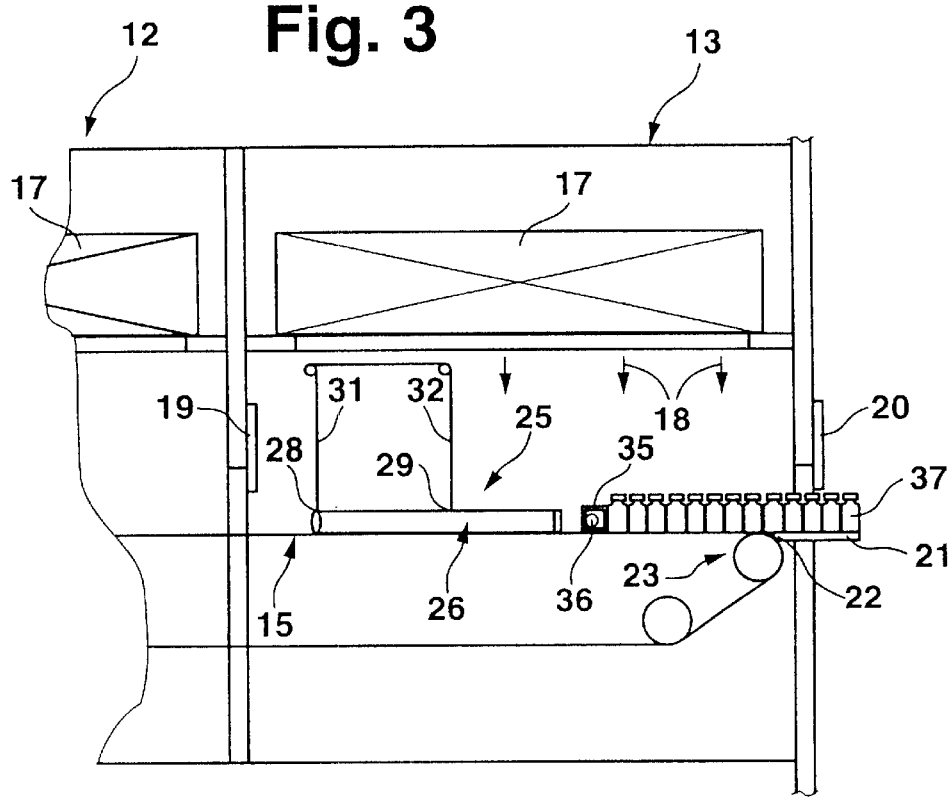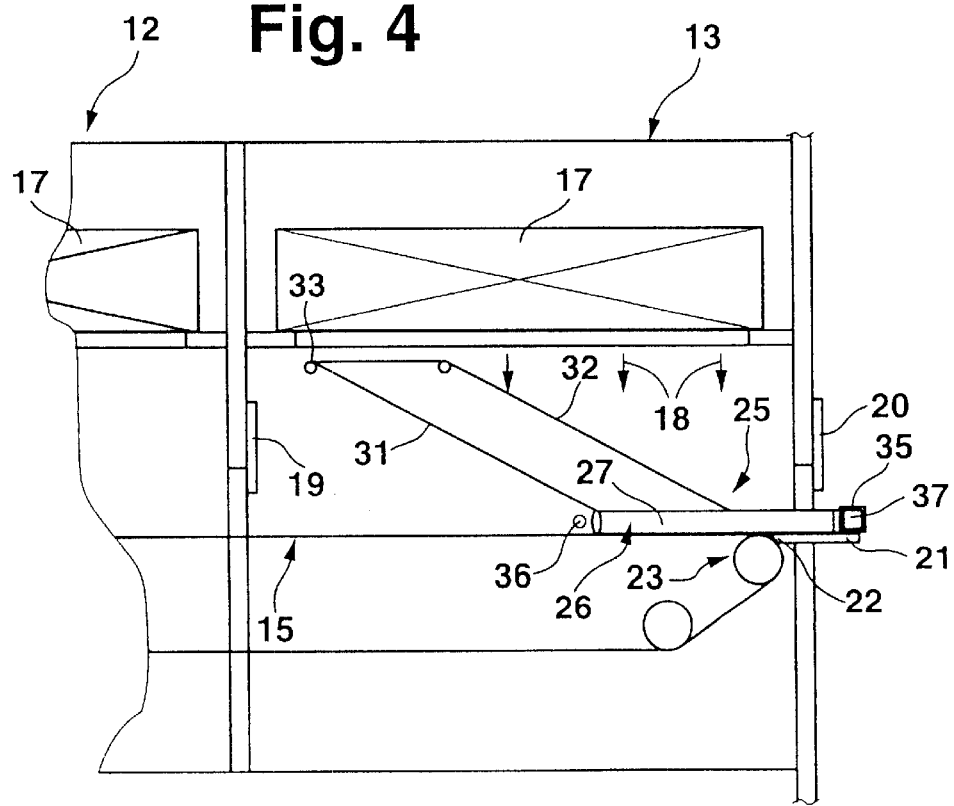

STERILIZATION TUNNEL

PRIOR ART

The invention relates to a sterilization tunnel in which sterilized containers are removed after each batch is run. After the passage of a batch of containers or at the end of a production shift, a sterilization tunnel of this kind must be emptied in order to assure that upon resuming production, packaging containers of a previous batch that could have become contaminated in the meantime are no longer disposed in the sterilization tunnel. To that end, as a rule, at the end of the container flow in the inlet zone of the sterilization tunnel, a bar-shaped emptying slider is placed onto the transport device for the containers, which is embodied as a conveyor belt, and pushes the containers or container parts disposed in front of it through the sterilization tunnel. Of critical importance, however, is the outlet region inside the sterilization tunnel before its outlet chute, at which the containers are transferred from the reversal region of the transport device onto an output plate. At this point, the emptying slider and the containers disposed in front of it come to a stop because the slider is not moved farther by any subsequent element. There are known, expensive mechanical embodiments such as ejection rakes or the like, which must be introduced into the outlet region of the sterilization tunnel from the outside in order to completely eject the emptying slider and the remaining containers. In order to prevent a contamination in outlet regions that can be sterilized, it is therefore often necessary, depending on the type of structural embodiment, to sterilize these parts before introduction into the outlet region.

ADVANTAGES OF THE INVENTION

The sterilization tunnel according to the invention has the advantage over the prior art that the emptying of the sterilization tunnel can take place manually or automatically in a particularly simple manner. Since no parts have to be introduced into the sterilization or cooling zone of the sterilization tunnel, the result is a particularly simple operation because no parts have to be additionally pre-sterilized.

Other advantages and advantageous improvements of the sterilization tunnel according to the invention ensue from the dependent claims and the description.

BRIEF DESCRIPTION OF THE DRAWINGS

An exemplary embodiment of the invention is shown in the drawings and will be explained in detail below.

FIG. 3 shows a further enlarged sectional view of the sterilization tunnel at another processing stage; and FIG. 4 shows a further enlarged sectional view of the sterilization tunnel at another processing stage.

DESCRIPTION OF THE EXEMPLARY EMBODIMENTS

Figure 1:
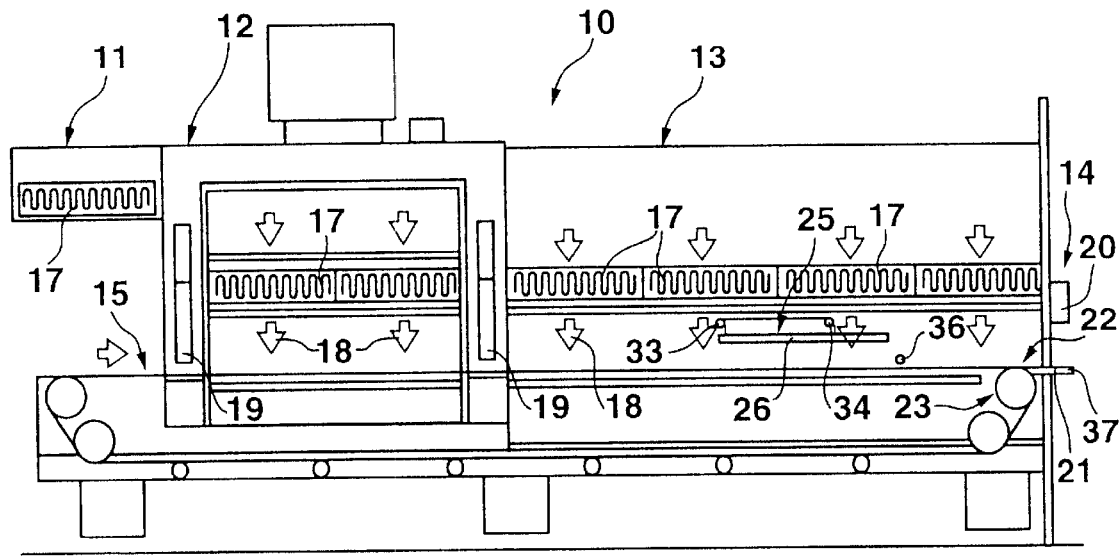
FIG. 1 is a simplified longitudinal section through a sterilization tunnel.

The sterilization tunnel 10 schematically depicted in FIG. 1 is essentially comprised of an inlet zone 11, a sterilization zone 12, and a cooling zone 13. Pharmaceutical containers such as ampules, vials 1, or the like come from a cleaning machine, are conveyed into the inlet zone 11 of the sterilization tunnel 10, and leave the tunnel on its opposite end 14 after the cooling zone 13 in order to be processed further in subsequent filling and closing machines which are not shown.

A horizontally revolving, endless conveyor belt 15 is used to transport the vials 1 through the individual zones inside the sterilization tunnel 10. In actual use, such conveyor belts are embodied as air-permeable wire mesh belts made of stainless steel. Large filter elements 17 are disposed above the conveyor belt 15 in the different zones of the sterilization tunnel 10 and direct air currents 18, which are heated by heating devices and produced by ventilators that are not shown, in such a way that the air currents 18, as so-called laminar flow currents, flow around the vials 1 perpendicular to the transport direction and are then recirculated. Since the air currents 18 have different temperatures in the individual zones, wherein the temperature is the highest in the sterilization zone 12, vertically adjustable intermediary walls 19 are disposed between the zones in order to reduce or prevent an overflow of the different temperature air between the individual zones.

A transfer plate 21 is disposed in the vicinity of the end 14 of the cooling zone 13, underneath a likewise vertically adjustable exit chute 20. The transfer plate 21 protrudes with its one end 22 into the immediate vicinity of the reversal region 23 of the conveyor belt 15 inside the sterilization tunnel 10. The end of the transfer plate 21 protruding from the sterilization tunnel 10 is adjoined by a transport device, not shown, of the filling and closing machine mentioned above.

An emptying device 25 disposed inside the cooling part 13 of the sterilization tunnel 10 is essential to the invention. The emptying device 25 has a frame 26 that extends in a horizontal plane and is preferably embodied of streamlined profiled rods 27 in order to resist or interrupt the laminar air flow 18 prevailing in the cooling zone 13 as little as possible. In the exemplary embodiment, the profiled rods 27 form a rectangular frame. The frame 26 has four suspension points 28, 29, of which the two front suspension points 28 are disposed in the vicinity of the corners on the end of the frame 26 opposite the end 14. The other two suspension points 29 are disposed approximately in the center of the frame 26, wherein the center of gravity of the frame 26, however, is disposed between the suspension points 28, 29. Wires 31, 32 or steel belts are fastened to the suspension points 28, 29. The wires 31 associated with the front suspension points 28 are connected to a shaft 33, which is disposed underneath the filter elements 17 of the cooling zone 13 on the end oriented toward the sterilization zone 12. The shaft 33 is coupled to a drive mechanism, not shown, which permits the shaft 33 to rotate in both directions. The wires 32 associated with the other suspension points 29 are also connected to the shaft 33. These wires 32, however, are conveyed around an axle 34 disposed underneath the filter elements 17 and parallel to the shaft 33. The lengths of the wires 31, 32 are matched to one another so that the frame 26 can be lowered or raised in parallel fashion when the shaft 33 is rotated.

Figure 2:
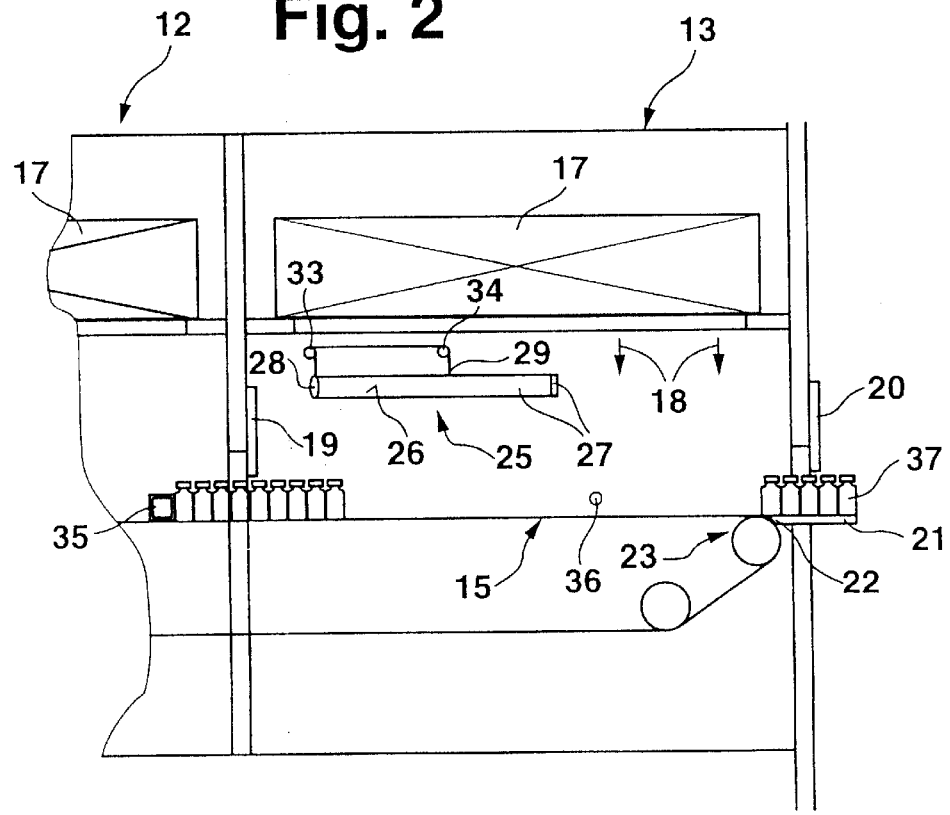
FIG. 2 shows an enlarged sectional view in greater detail of the sterilization tunnel.

The emptying device 25 described above functions as follows: after the last vials 1 of a batch has been supplied to the inlet zone 11 of the sterilization tunnel 10, or at the end of a production shift, a bar-shaped emptying slider 35 which covers the conveyor belt 15 laterally is placed after the last vials 1. This emptying slider 35, together with the last vials 1, is conveyed by the conveyor belt 15 through the sterilization tunnel 10 (FIG. 2). Preferably, as soon as the emptying slider 35 is disposed at a particular point underneath the frame 26, which is detected by means of a first sensor 36 coupled to the control unit of the sterilization tunnel 10, the lowering of the frame 26 is begun by means of a corresponding rotation of the shaft 33. In the most favorable instance, the frame 26 lowered onto the conveyor belt 15 comes almost immediately after the emptying slider 35 (FIG. 3).

As soon as the frame 26 has been lowered onto the conveyor belt 15, the shaft 33 is uncoupled from its drive mechanism or the drive mechanism is switched off so that the frame 26 can be carried along by the conveyor belt 15 without the distance from the emptying slider 35 increasing. Since the frame 26 has a certain mass and since a high static friction factor prevails between the frame 26 and the conveyor belt 15, which can for example be increased further by means of a coating on the underside of the frame 26, the leading end of the frame 26 pushes the emptying bar 35, together with the vials 1 disposed in front of it, over the reversal region 23 of the conveyor belt 15 onto the transfer plate 21 and through the exit chute 20 of the cooling zone 13 (FIG. 4). Since the suspension points 29 are not disposed in the free corners of the frame 26 but approximately in its center, it is possible that the leading end of the frame 26 passes through the exit chute 20 without the exit chute 20 having to be raised because of the wires 32.

As soon as the emptying bar 35 has been slid through the exit chute 20 by the frame 26, which can be detected by means of a second sensor 37 coupled to the control unit of the sterilization tunnel 10, the drive mechanism of the transport belt 15 should be switched off or even operated in the reverse direction in order to facilitate the subsequent return of the frame 26 into its original, raised position. During this returning process, the shaft 33 is now rotated in the opposite direction. As a result, the wires 31, 32 wind onto the shaft 33 and lift the frame 26 from the conveyor belt 15 as soon as the suspension points 28, 29 are disposed beneath the shaft 33 and the axle 34.

The foregoing relates to a preferred exemplary embodiments of the invention, it being understood that other variants and embodiments thereof are possible within the spirit and scope of the invention, it latter being defined by the appended claims.

We claim:

1. A sterilization tunnel (10), comprising a transport device which supplies pharmaceutical containers, (1) through an inlet zone (11), a sterilization zone (12), and a cooling zone (13), which is embodied as an endless conveyor belt (15) with a reversal region (23) disposed in the cooling zone (13), with a transfer element (21) adjoins the reversal region (23) upon which the pharmaceutical containers (1) slide along because of the dynamic pressure of the containers (1) subsequently supplied on the conveyor belt (15), the transfer element (21) passes through the cooling zone (13) in the vicinity of a chute (20) with an emptying slider (35) that covers the conveyor belt (15) laterally, the emptying slider can be fed through the zones (11, 12, 13) by the conveyor belt (15) in order to empty the sterilization tunnel (10) and with means for conveying the emptying slider (35) further through the chute (20), a device (25) that can be raised and lowered and used to eject the emptying slider (35) from the cooling zone (13) is disposed above the conveyor belt (15) and for the ejection, the device (25) can be lowered onto the conveyor belt (15), which brings the device (25) into contact with the emptying slider (35) and then pushes the slider onto the transfer element (21) and through the chute (20).

2. The sterilization tunnel according to claim 1, in which the device (25) is disposed beneath filter elements (17) in an air flow (18) directed perpendicular to the feed direction of the containers (1) and has a frame (26) comprised of rods (27).

3. The sterilization tunnel according to claim 2, in which the device (25) has suspension points (28, 29) for wire elements (31, 32) that can be wound and unwound by means of at least one shaft (33) coupled to a drive mechanism.

4. The sterilization tunnel according to claim 1, in which the device (25) has suspension points (28, 29) for wire elements (31, 32) that can be wound and unwound by means of at least one shaft (33) coupled to a drive mechanism.

* * * * *